United States Patent [19]
Shirley

[11] Patent Number: 6,110,138
[45] Date of Patent: Aug. 29, 2000

[54] STANCE-CORRECTING KNEE BRACE

[75] Inventor: Terry L. Shirley, Laguna Hills, Calif.

[73] Assignee: Tagg Industries, L.L.C., Laguna Hills, Calif.

[21] Appl. No.: 09/241,323

[22] Filed: Feb. 1, 1999

[51] Int. Cl.[7] .................................................. A61F 5/00
[52] U.S. Cl. ............................................. 602/26; 602/16
[58] Field of Search ................................... 602/5, 16, 23, 602/26; 482/124; 607/23, 32, 36

[56] References Cited

U.S. PATENT DOCUMENTS

| | | | |
|---|---|---|---|
| 2,195,024 | 3/1940 | Bullock | 602/26 |
| 3,804,084 | 4/1974 | Lehman | 602/26 |
| 4,433,679 | 2/1984 | Mauldin et al. | 602/26 X |
| 4,697,583 | 10/1987 | Mason et al. | 602/26 |
| 4,791,916 | 12/1988 | Palz | 602/16 X |
| 4,887,590 | 12/1989 | Loque et al. | 602/26 |
| 4,941,462 | 7/1990 | Lindberg | 602/26 |
| 4,986,263 | 1/1991 | Dickerson et al. | 602/26 |
| 4,986,264 | 1/1991 | Miller | 602/26 X |
| 5,002,045 | 3/1991 | Spademan | 602/26 X |
| 5,013,037 | 5/1991 | Sterner | 602/26 X |
| 5,167,612 | 12/1992 | Bonnuti | 602/16 X |
| 5,599,288 | 2/1997 | Shirley et al. | . |
| 5,662,595 | 9/1997 | Chester et al. | 602/20 |
| 5,857,988 | 1/1999 | Shirley | . |

*Primary Examiner*—Richard J. Apley
*Assistant Examiner*—Kim M. Lee
*Attorney, Agent, or Firm*—Harry G. Weissenberger

[57] ABSTRACT

Pain associated with unicompartmental osteoarthritis is relieved, and external varus or valgus movement about the knee is counteracted, by a soft brace in which a single cable pulled downwardly around the front of the femoral area adjacent the knee in one directon, and downwardly around the front of the tibial area adjacent the knee in the opposite direction, exerts a lateral force on the thigh and calf in one direction, and against the knee in the opposite direction.

4 Claims, 6 Drawing Sheets

STANCE-CORRECTING KNEE BRACE

FIELD OF THE INVENTION

This invention relates to orthopedic braces, and more particularly to a lightweight knee brace capable of correcting abnormal stances and relieving unicompartmental osteoarthritis pain.

BACKGROUND OF THE INVENTION

U.S. Pat. Nos. 5,599,288 and 5,857,988 disclose knee braces using cross-connected cables to stabilize the knee and its ligaments and keep them aligned in patients with knee injuries. Because of the bilateral nature of the cross-connected cable design which distributed the stabilizing forces essentially evenly on both sides of the knee, these braces were, however, not effective in treating unicompartmental osteoarthritis pain or correcting stance abnormalities such as knock-kneed (valgus) or bowlegged (varus) stances of the otherwise healthy legs of children and adolescents, or in treating patients with medial or lateral unicompartmental osteoarthritis.

Currently available braces designed to correct such problems are heavy, expensive and awkward. It would therefore be desirable to be able to use the light, inexpensive bracing technology of the above-mentioned patents for this purpose.

SUMMARY OF THE INVENTION

The present invention makes it possible to correct stance abnormalities and treat unicompartmental osteoarthritis through the use of the cable technology of the above-identified patents by using only a single cable extending from an anchor point on the side of the thigh toward which the knee needs to be moved, to a point on the opposite side of the leg at the knee, and back again to an anchor point on the first-mentioned side of the calf. By tightening the cable at the anchor points, a desired amount of turning stress can be applied to the leg. Over a period of time, this constant stress will gradually straighten the patient's leg.

DESCRIPTION OF THE PREFERRED EMBODIMENT

Figure 1:
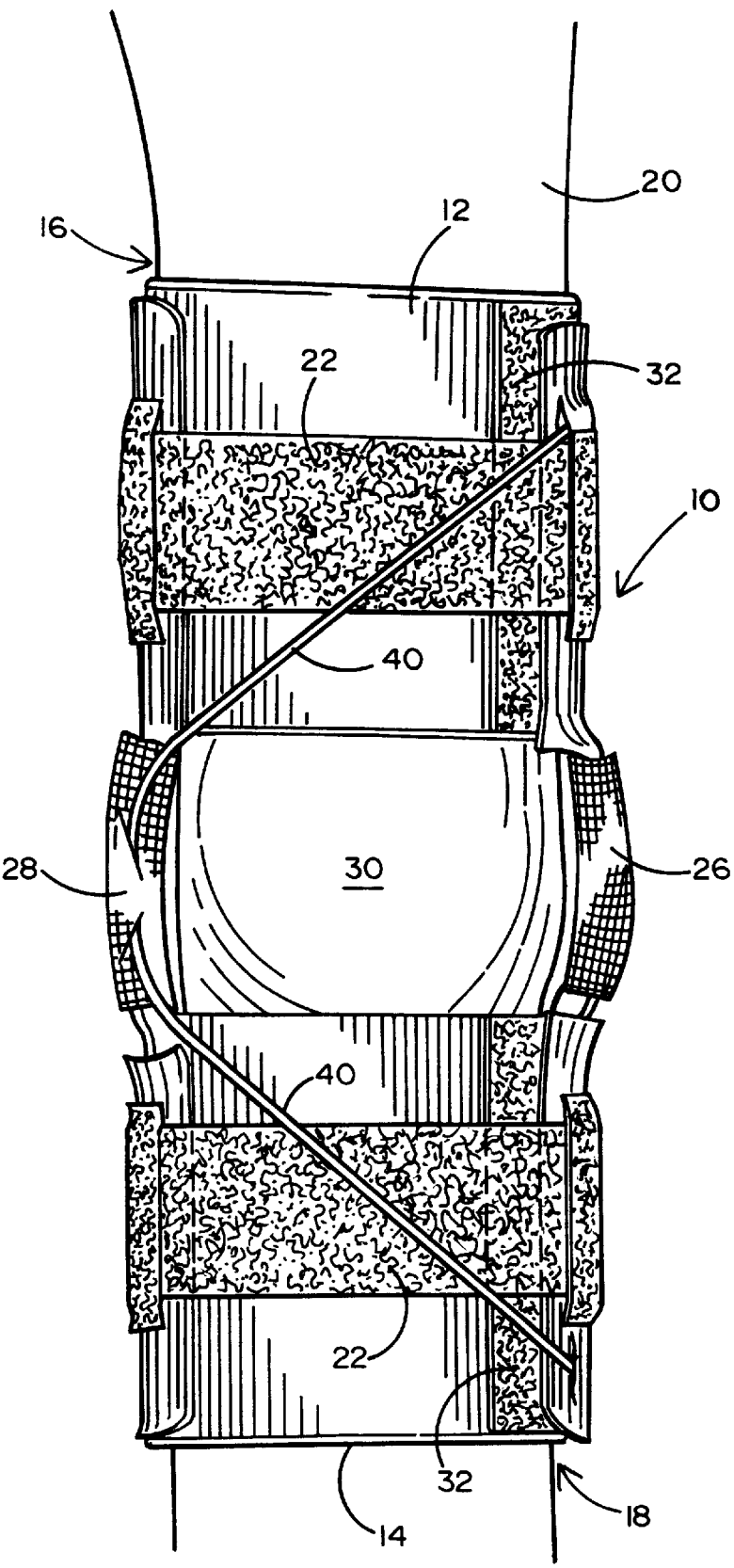
FIG. 1 is a front elevation of the inventive brace installed on a patient's leg.
Figure 2:
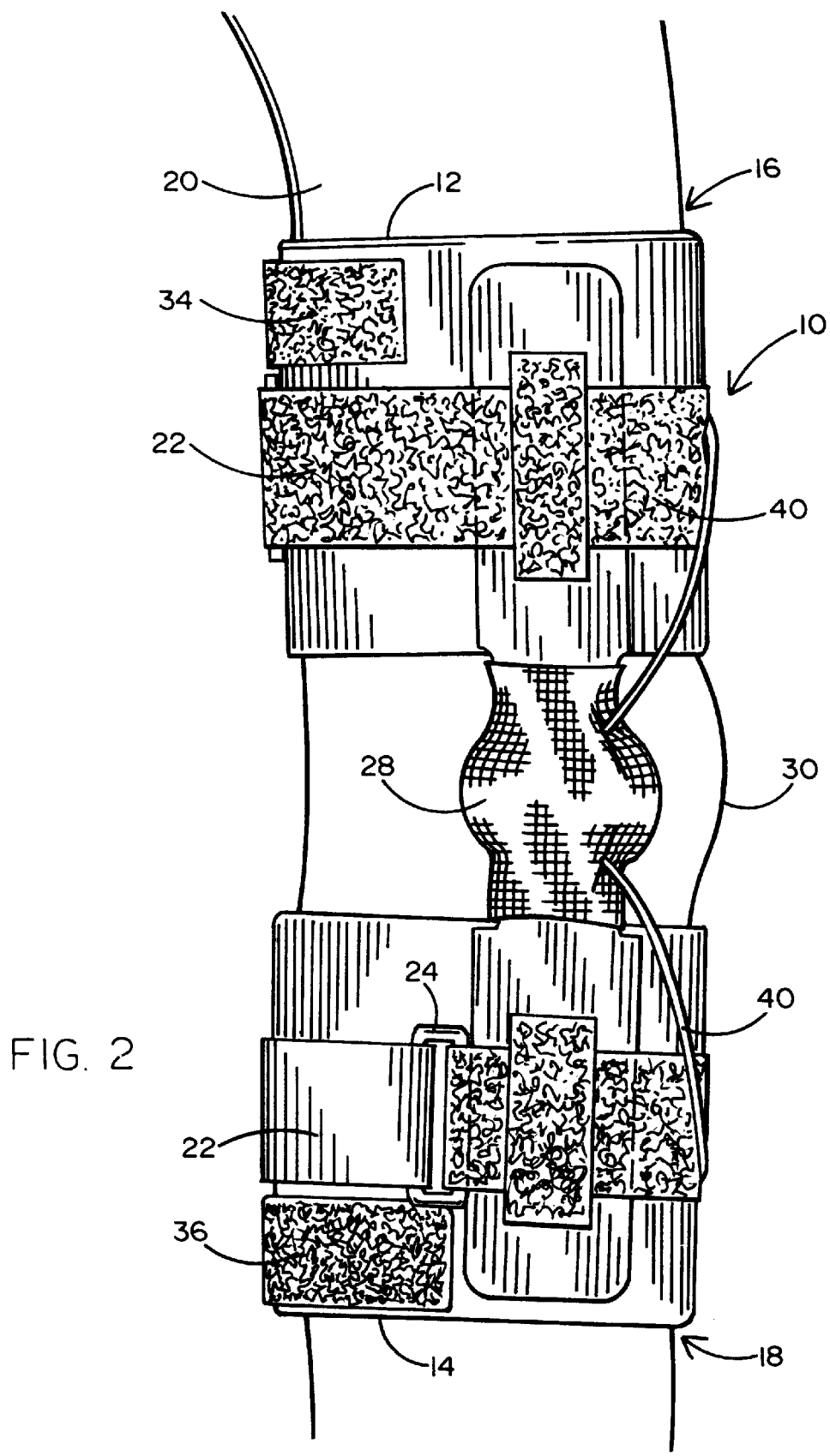
FIG. 2 is a right side elevation of the same.
Figure 3:
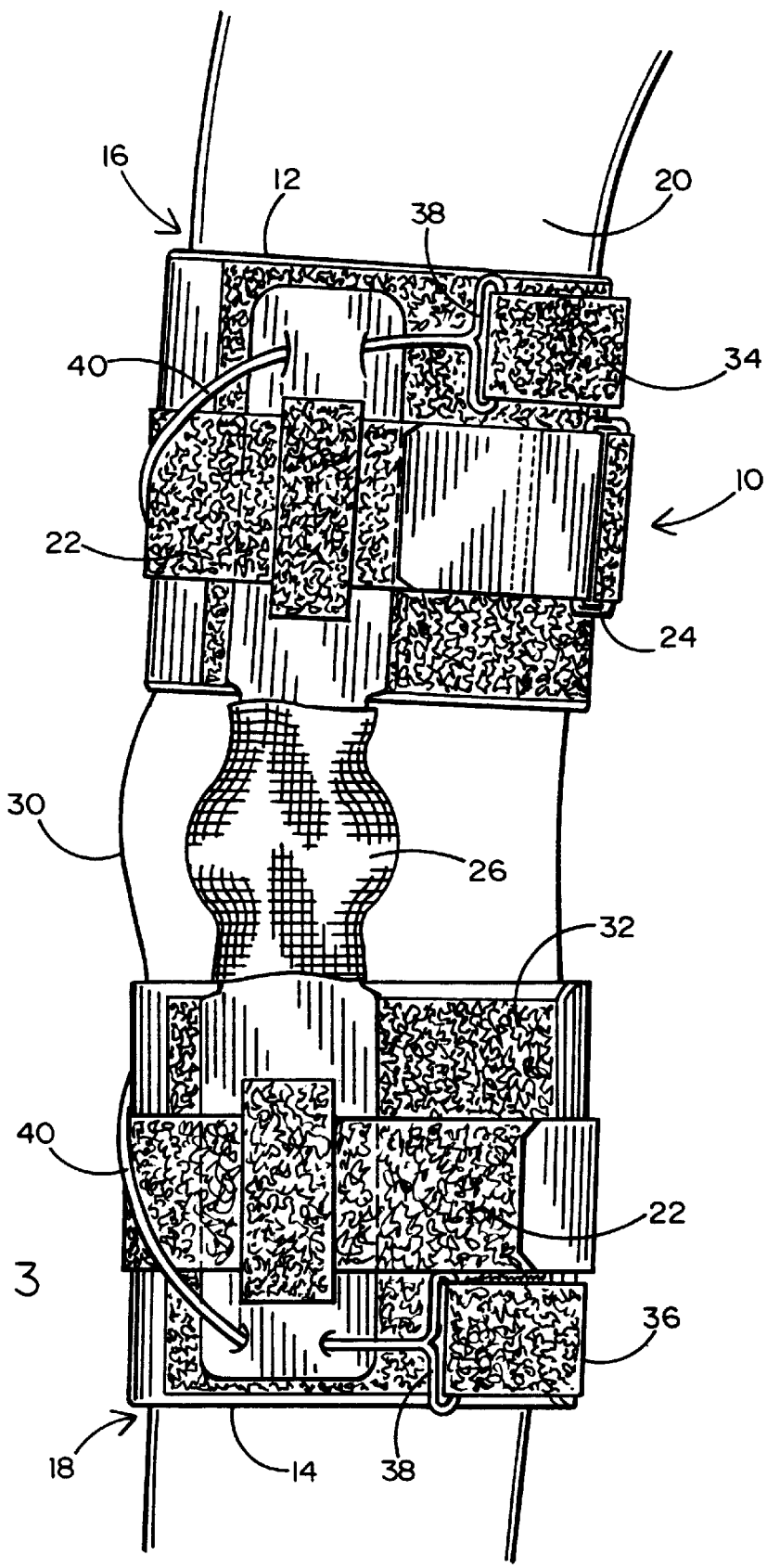
FIG. 3 is a left side elevation of the same.
Figure 4:
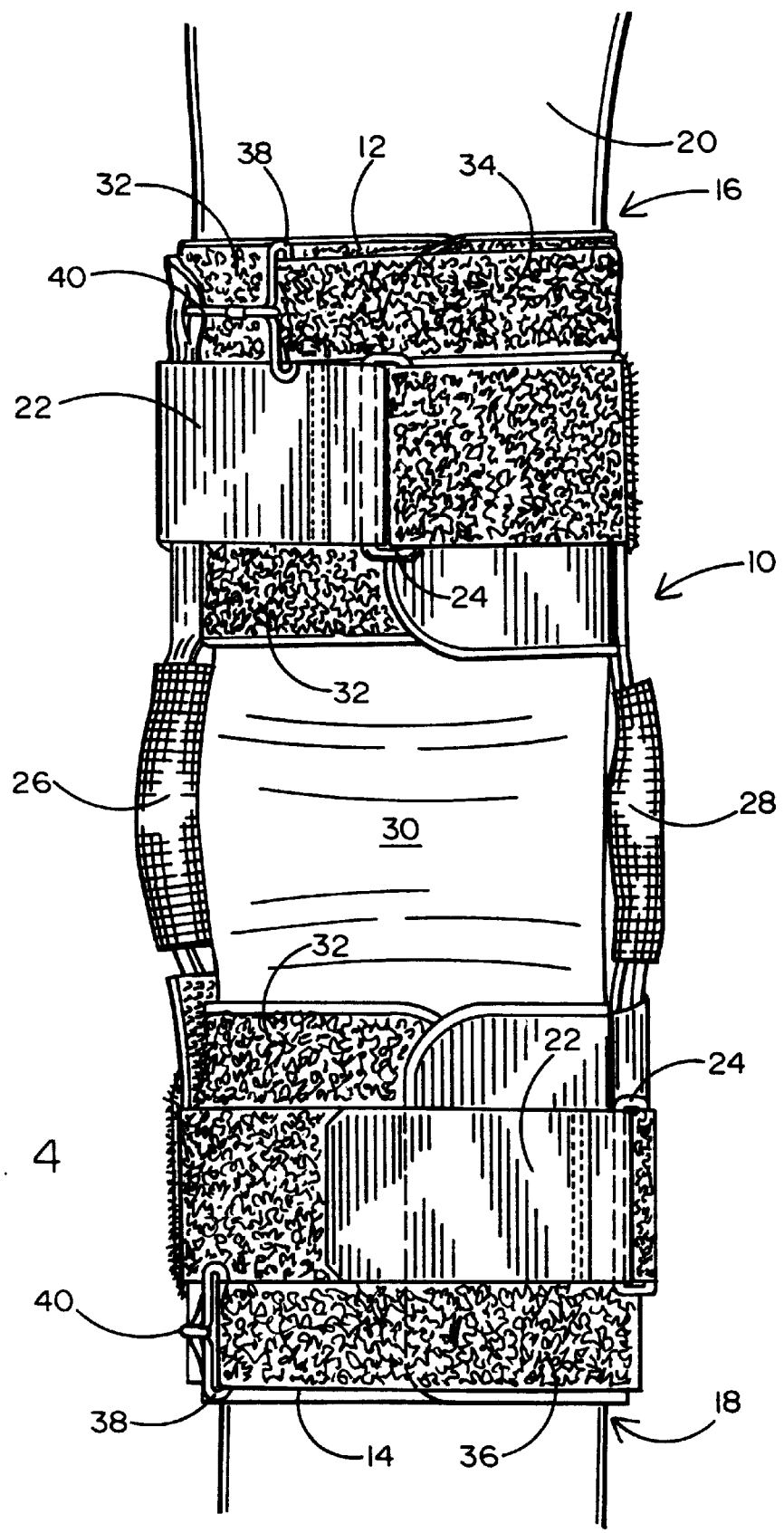
FIG. 4 is a rear elevation of the same.

The brace 10 of this invention includes a pair of lightweight cuffs 12, 14 formed of a soft, flexible material so as to comfortably encircle the femoral area 16 and tibial area 18, respectively, of the leg 20. The cuffs 12, 14 are preferably substantially rectangular sheets that are wrapped around the thigh and calf of the leg 20 and are held on the leg 20 by an adjustable band 22 secured by a clip 24.

When the cuffs 12, 14 are correctly positioned on the leg 20, the hinged linkages 26, 28, which are attached to the cuffs 12, 14 as shown in the figures, are positioned on each side of the knee 30. The hinge axes of the linkages 26, 28, when properly positioned, should coincide with each other and with the flexure axis of the knee 30. The linkages 26, 28 may, if desired, include stops (not shown) to limit the flexion and extension of the knee 30. The hinges of the linkages 26, 28 may be covered with a protective sleeve as shown in FIGS. 1–4 and 6.

The exterior portions 32 of the cuffs 12, 14 are provided with a Velcro surface. This surface engages the complementary Velcro surface formed on the inside of cable straps 34, 36. The cable straps 34, 36 are attached by hooks 38 to the upper and lower end, respectively, of a cable 40. The cable 40 is preferably a steel cable coated with plastic for softness and cleanability.

To activate the corrective action of the brace 10, the cable strap 34 is secured to the Velcro surface of the cuff 12, and the cable 40 is then pulled tight by pulling the cable strap 36 around the back of the tibial area 18 and securing it to the Velcro surface of cuff 14.

Figure 5A:
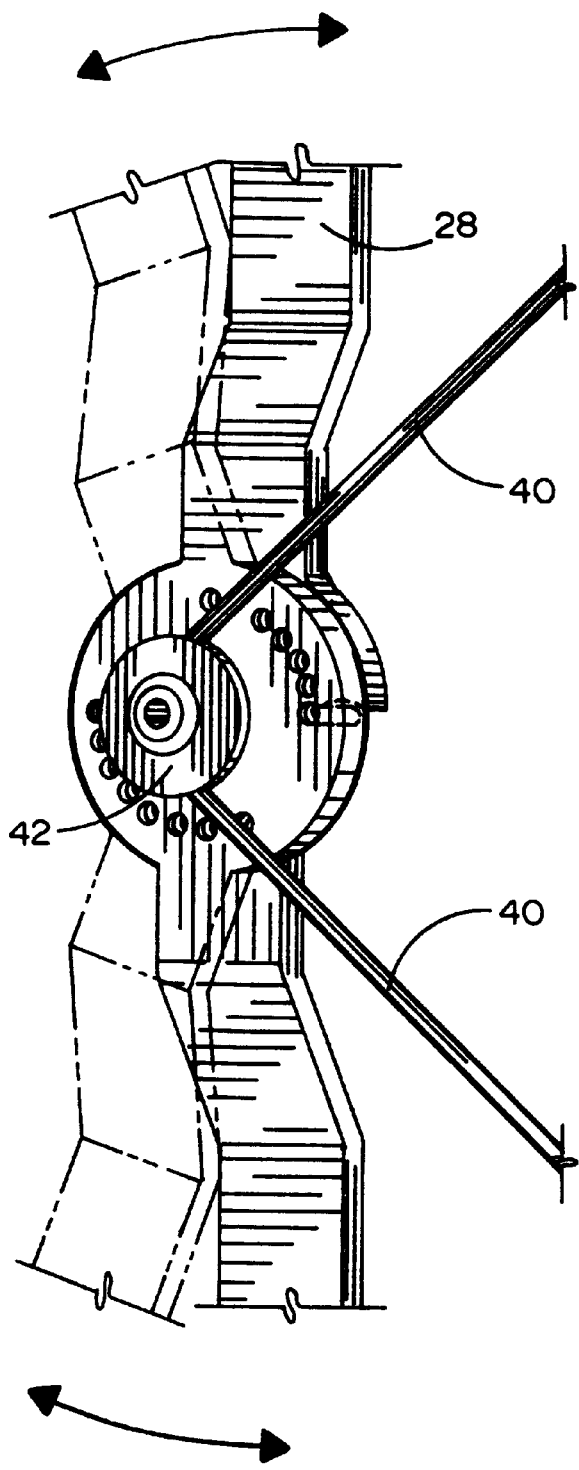
FIG. 5a is a detail perspective view.
Figure 5B:
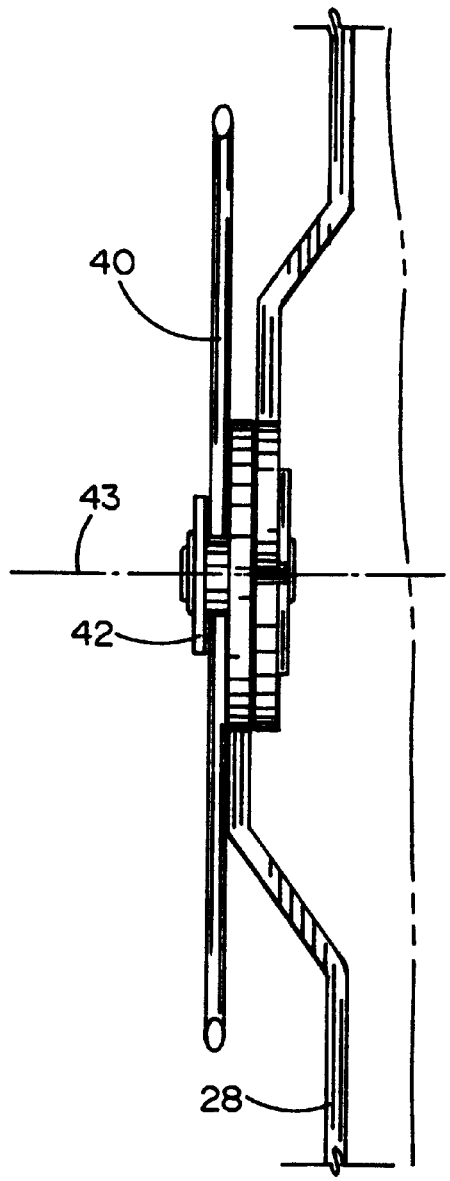
FIG. 5b a side view, of a linkage.

When so tightened, the cable 40 extends from the hook 38 on the right side (in FIG. 1) of the leg 20 across the front of the femoral area 16, around the pulley 42 (FIG. 5b) which is coaxial with the hinge axis 43 of linkage 28 on the left side (in FIG. 1) of the knee 30, and across the front of the tibial area 18 to the hook 38 on the right side (in FIG. 1) of the leg 20.

With the cable 40 installed in this manner, the hooks 38 serve as anchoring devices for the cable 40, and the cuffs 12, 14 serve as supports for those anchoring devices. It will be understood that although cuffs 12, 14 are shown herein as separate devices, they may be joined as illustrated in U.S. Pat. No. 5,599,288 to form a continuous sheath extending from the femoral area 16 to the tibial area 18.

Figure 6:
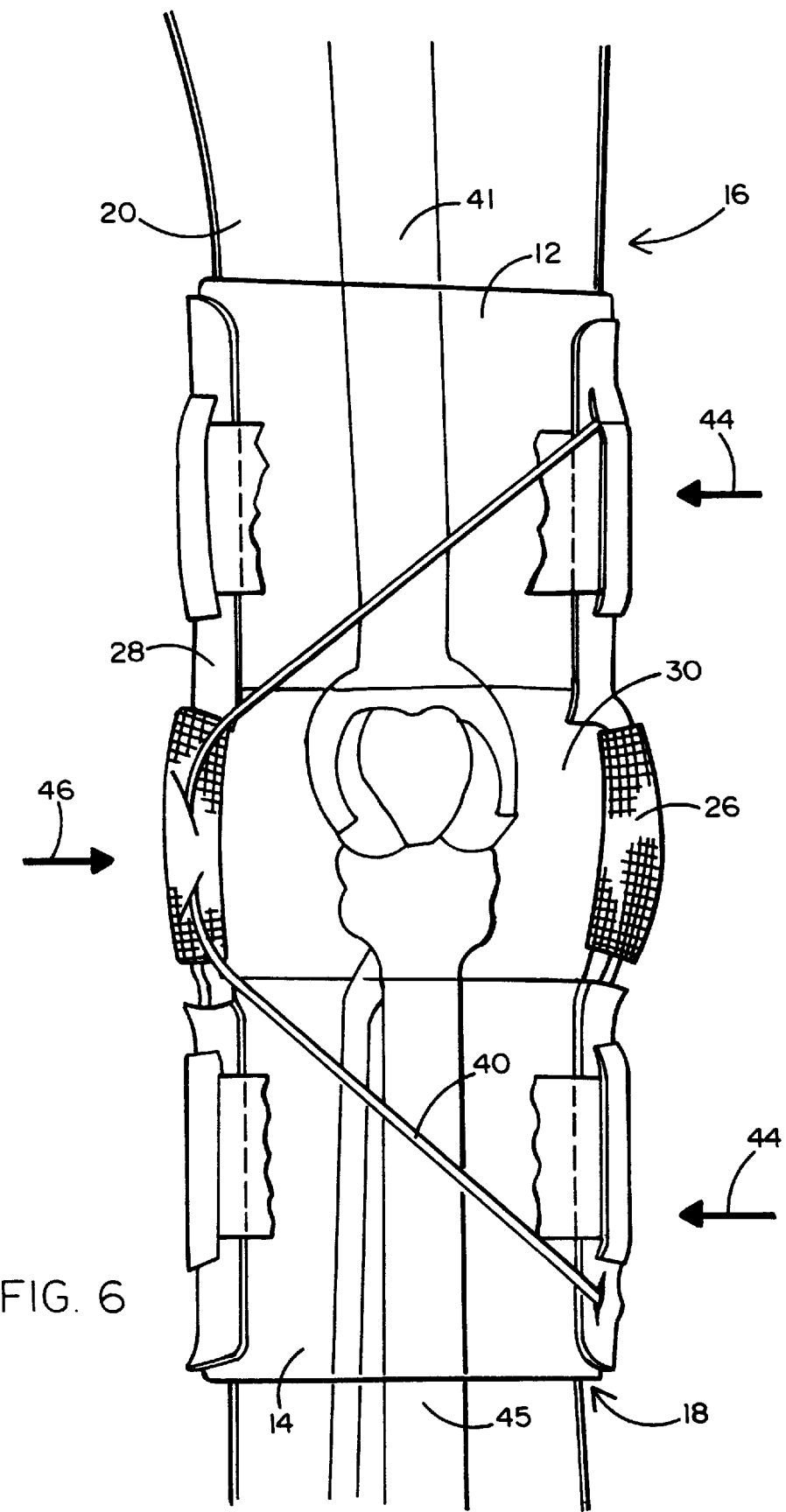
FIG. 6 is a schematic diagram illustrating the forces applied to the leg by the inventive brace.

FIG. 6 shows the forces exerted on the leg 20 and its femur 41 and tibia 45 by the described arrangement of cable 40. While the femoral area 16 and the tibial area 18 are pulled to the left (arrows 44), the knee 30 is pulled to the right (arrow 46). The interplay of these forces can relieve the pain of unicompartmental osteoarthritis and can, over a period of time, promote a straightening of the leg.

An additional advantage of the soft, comfortable open cell urethane stretch material which preferably forms the cuffs 12, 14 is that it holds in the body heat of the leg 20, and thus keeps the femoral and tibial muscles adjacent to the knee 30 warm and supple.

The left-right orientation of the cable can be reversed from the orientation shown in the figures to accommodate left or right legs, and varus or valgus abnormalities.

It is understood that the exemplary stance-correcting knee brace described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A method of treating stance abnormalities of the varus and valgus types, comprising the steps of:

a) securing a first cable anchoring device to a first support surrounding a patient's leg in the femoral area of the leg;

b) securing a second cable anchoring device to a second support surrounding said patient's leg in the tibial area of the leg;

c) connecting said supports on a first side of the leg by a rigid linkage including a hinge having a hinge axis substantially coincident with the flexure axis of the knee of the leg;

d) providing a single cable;

e) securing one end of said cable to said first anchoring device on a second side of said leg opposite said first side;

f) securing the other end of said cable to said second anchoring device on said second side of the leg;

g) positioning said cable to extend from said first anchoring device to said hinge across the front of the leg, and from said hinge to said second anchoring device across the front of the leg; and h) tightening said cable so as to pull said hinge toward said anchoring devices.

2. The method of claim 1, in which said supports are cuffs placed around the leg, and said anchoring devices are cable hooks movably attached to said cuffs.

3. A stance-correcting knee brace, comprising:

a) a first support adapted to surround a patient's leg in the femoral area of the leg;

b) a second support adapted to surround a patient's leg on the tibial area of the leg;

c) a rigid linkage connecting said supports on a first side of the leg, said linkage including a hinge having a hinge axis substantially coincident with the flexure axis of the knee of the leg;

d) a first cable anchoring device secured to said first support on a second side of the leg opposite said first side;

e) a second cable anchoring device secured to said second support on said second side of the leg; and f) a single cable extending from said first anchoring device to said hinge across the front of the leg, and from said hinge to said second anchoring device across the front of the leg;

g) said anchoring devices being arranged to allow said cable to be tensioned.

4. The knee brace of claim 3, in which said hinge includes a pulley, and said cable is positioned around said pulley at said hinge.

* * * * *